US005679864A

United States Patent [19]

Krackov et al.

[11] Patent Number: 5,679,864

[45] Date of Patent: Oct. 21, 1997

[54] PROCESS FOR THE SYNTHESIS OF CURCUMIN-RELATED COMPOUNDS

[75] Inventors: Mark Harry Krackov, West Chester, Pa.; Harold Edward Bellis, Wilmington, Del.

[73] Assignee: Gene Print Inc., Bala Cynwyd, Pa.

[21] Appl. No.: 552,904

[22] Filed: Nov. 3, 1995

[51] Int. Cl.[6] .......... C07C 45/00

[52] U.S. Cl. .......... 568/313

[58] Field of Search .......... 568/313

[56] References Cited

FOREIGN PATENT DOCUMENTS

| | | |
|---|---|---|
| 859145 | 12/1952 | Germany . |
| 1280849 | 10/1968 | Germany . |
| 1282642 | 11/1968 | Germany . |
| 914047 | 8/1959 | United Kingdom . |

OTHER PUBLICATIONS

Antonio F. Arrieta, Direct Synthesis of Demethoxycurcumin, *C.R. Acad. Sci.* Paris, Ser II, 479–82, 1994.

Pedersen, et al., Synthesis of Naturally Occurring Curcuminoids and Related Compounds, *Ann. Chem.*, 1557–69, 1985.

Arrieta, et al., Synthesis and H-NMR–spectrospopic Investigatons of New Curcumin Analoga, *J. prakt. Chem.*, 334, 656–700, 1991.

Roughly, et al., Experiments in the Biosynthesis of Curcumin, *JCS Perkins Trans I*, I, 2379–88, 1973.

Chemical Abstracts Plus 1995:238262, Babu et al 1994.

*Primary Examiner*—Samuel Barts

[57] ABSTRACT

The invention is directed to a process for the synthesis of curcumin and curcumin-related compounds by reacting the enol form of a 2,4-diketone with a monocarbocyclic aldehyde in the presence of an organic amine catalyst. The reactants are dissolved in a highly polar, aprotic organic solvent. The curcumin-related product is recovered in crystalline form by precipitation from the reaction mass and solvent recrystallization.

17 Claims, No Drawings

PROCESS FOR THE SYNTHESIS OF CURCUMIN-RELATED COMPOUNDS

FIELD OF THE INVENTION

The invention is directed to a process for the synthesis of curcumin and homologs and analogs thereof.

BACKGROUND OF THE INVENTION

Curcumin [1,7-bis(4-hydroxy-3-methoxyphenyl)-1,6-heptadiene-3,5-dione] is a naturally occurring compound which is the main coloring principle found in the rhizomes of the plant *Curcuma longa*. This natural pigment is widely used as a coloring agent in foods and cosmetics and is reported to have various pharmaceutical uses. Among these are its action as a bile-secretion stimulating agent, as an anti-inflammatory agent and as an antioxidant. It is also reported to be a potent inhibitor of certain skin and internal cancer growths.

The isolation of natural curcumin from the *Curcuma longa* rhizome is a difficult and costly procedure. No practical way has been found to effect separation of curcumin itself from two related demethoxy compounds with which it is found in nature. This difficulty of separation has led to several attempts to synthesize the compound, the most important of which has been aldol condensation of vanillin (3-methoxy-4-hydroxybenzaldehyde) and 2,4-pentanedione. However, the yields of product from these syntheses have heretofore been very low, in large part because of the difficult and complicated procedures required for isolation and purification of the product.

Among the procedures utilizing the above described general processes are the reaction of vanillin and the boron complex of 2,4-pentanedione dissolved in ethyl acetate in the presence of tri-n-butyl borate and a primary aliphatic amine. Another similar procedure is the reaction of vanillin and the boron complex of 2,4-pentanedione dissolved in dimethyl sulfoxide. However, the product of this latter procedure is an extremely viscous reaction mass which, upon hydrolysis, forms a dark colored, glassy tar. In a still further procedure, the reaction is carried out without a solvent. In all of these procedures, the yields or process operability are poor. Separation of the curcumin from the tar-like by-products has proven to be extremely difficult.

Such prior methods for making curcumin are illustrated in the following publications:

Graf, German Preliminary Published Patent 1,280,849, published Oct. 24, 1968;

Graf, German Preliminary Published Patent 1,282,642, published Nov. 14, 1968;

Sieglitz et at., German Patent 859,145, issued Dec. 11, 1952; and

Roughly et al., *JCS Perkins Trans I*, 1973, p. 2379–88

Peterson et al., *Ann.*, 1985, p. 1557–69

Arrieta et al., *J. Prakt Chem.*, 334, 1991, p. 656–700

Arrieta et al., *Acad. Sci. Paris Ser. II*, 1994, p. 479–82

SUMMARY OF THE INVENTION

In its primary aspect, the invention is directed to a novel method for the synthesis of curcumin and curcumin-related compounds in high yields with improved methods for separation of reaction products.

More particularly, the invention is directed to a process for the synthesis of curcumin-related compounds comprising the sequential steps:

A. In a chemically inert, highly polar, aprotic solvent, reacting a suitable complexing agent with a 2,4-diketone of the general structure $RCH_2$—CO—$CH_2$—CO—$CH_2R$ in order to produce a stable enolic reactant with the general structure $RCH_2$—C(OH)=CH—CO—$CH_2R$ in which the R groups are independently selected from H and $C_{1-12}$ hydrocarbyl groups selected from alkyl, aryl, aralkyl, alkaryl groups and mixtures thereof;

B. To the reaction from step A, adding aromatic aldehyde in sufficient amount to effect complete reaction of all of the intermediate enolic diketone in the solution;

C. Admixing with the liquid solution from step B, a catalyst selected from the group consisting of organic primary amines, secondary amines and mixtures thereof to effect aldol condensation of the aldehyde with the terminal alpha carbon atoms of the enolic alkyl diketone with the concomitant formation of curcumin-related compound, intermediate compounds, water and other reaction by-products and continuing the reaction until all of the enolic alkyl diketone in the reaction mass has been consumed;

D. Admixing the reaction mass from step C with dilute aqueous acid to effect hydrolysis of the complex neutralization of any organic amine catalyst which is present, precipitation of curcumin-related compound in crystalline form and solubilization of unreacted materials; and E. Separating the precipitated crystals of curcumin-related compound from the unreacted materials solubilized in Step D.

DEFINITIONS

As used herein the following terms have the indicated meanings:

The term "curcumin-related compound" refers to 1,7-diaryl-1,6-heptadiene-3,5-diones, which are curcumin-related compounds which can be made by the process of the invention. The term includes homologs and analogs of such compounds.

The term "complex" refers to stable enolic configurations of the alkyl diketone reactant. Such enolic stability is usually accomplished by formation of a complex of the alkyl diketone with a complexing agent.

The term "water scavenger" refers to a material which combines irreversibly with water contained or formed in the reaction mass either physically or chemically in such manner that the resultant combination is inert with respect to other components of the reaction mass.

DETAILED DESCRIPTION OF THE INVENTION

Primary Reactants

The primary reactants for the process of the invention are 2,4-diketones and aromatic aldehydes. The diketones suitable for use in the process of the invention are those corresponding to the structural formula $H_2RC$—CO—$CH_2$—CO—$CRH_2$, in which the R groups are independently selected from H and $C_{1-12}$ hydrocarbyl groups selected from alkyl, aryl, aralkyl, alkaryl groups and mixtures. Acetylacetone, i.e. 2,4-pentanedione, is preferred for use in the invention.

Other suitable diketones include 3-substituted-2,4-pentanediones, $RCH(COCH_3)_2$, where R is $CH_2{=}CHCH_2$, $CH_3(CH_2)_3$, $(CH_3)_2CH$, $C_2H_5CO_2CH_2$, $C_2H_5O_2C(CH_2)_2$, $HO_2C(CH_2)_2$.

A wide variety of aromatic aldehydes are suitable for use in the invention, of which vanillin is preferred because it is a basic constituent of curcumin itself. However, derivatives and analogs of vanillin and other aromatic aldehydes can be used also.

Other suitable aromatic aldehydes include o-vanillin, veratraldehyde, 3-anisaldehyde, 2-anisaldehyde, p-anisaldehyde, 2-hydroxybenzaldehyde, 3-hydroxybenzaldehyde, 4-hydroxybenzaldehyde, syringaldehyde, 2-hydroxy-5-nitrobenzaldehyde, 3-hydroxy-4-nitrobenzaldehyde, 4-hydroxy-3-nitrobenzaldehyde, 2-nitro-5-hydroxybenzaldehyde, 3-fluoro-2-methylbenzaldehyde, 3-fluoro-4-methoxybenzaldehyde, 2-fluorobenzaldehyde, 3-fluorobenzaldehyde, 4-fluorobenzaldehyde, 3-fluoro-2-ethylbenzaldehyde and 3-fluoro-2-hydroxybenzaldehyde.

The stoichiometric ratio of aldehyde to diketone is theoretically 2:1. However, we have found that, due to depletion of the diketone by side reactions, only 87–89% of the aldehyde is consumed in the reaction of vanillin with 2,4-pentanedione. It is therefore possible to reduce the aldehyde/diketone molar ratio as low as 1.8:1.

To carry out the reactions of the invention, it is essential that the 2,4-diketones be present in the reaction system in the enol configuration. In order to avoid Knoevenagel condensation at C-3 of 2,4-pentanedione, it is necessary to protect C-3 by forming an enolic structure. Then the condensation will occur only on the terminal methyl groups.

The enol configuration is conveniently formed by complexing the diketone with boron or other metal complexing agents. Other approaches to forming the enol include the chemical conversion of the diketone into an enol ether, enol ester or 3,5-dimethylisoxazole prior to running the reaction.

Solvent

The appropriate selection of solvent for the process of the invention is most important. It must not only provide appropriate solubility for the reactants, intermediates and products, but it must also provide a medium of suitable polarity for the process. The effect of solvent on the effective base strength of the catalyst has quite unexpectedly been found to be important. (See discussion of catalyst below). Thus, the preferred catalyst compositions depend in part on the solvent used in the reaction. Furthermore, the preferred solvents must facilitate the isolation and separation of the curcumin product from tarry products which are inevitably part of the crude reaction product.

Suitable solvents for use in the invention include highly polar, aprotic solvents, especially organic amides such as N,N-dimethylacetamide, N,N-dimethylformamide, N-methylpyrrolidinone, N-formylpyrrolidine and the like. Even though it is highly polar and aprotic, dimethyl sulfoxide is not suitable for use in the invention because it forms a tarry mass from which the curcumin-related product is extremely difficult to separate except with excessive losses in yield.

Catalyst

The effective basicity of the catalyst is of critical importance. It must be strong enough to effect deprotonation of the acidic alkyl groups of the diketone; yet, it must not be so basic that deprotonation of the phenolic —OH groups occurs, which would result in deactivation of the aldehyde with respect to the condensation reaction between the diketone and the monocarbocyclic aldehyde. Furthermore, because of the relative instability of curcumin under basic conditions, which can lead to the formation of tarry higher molecular weight addition products, the amine catalyst for use in the invention must be chosen with care and the amount of catalyst in the system must be carefully regulated. In addition, because the basicity of the catalyst varies in different solvents, preferred catalysts are chosen in consideration of the particular solvents which are used.

Suitable catalysts for use in the process of the invention are primary and secondary amines such as morpholine, n-Butylamine, ethanolamine, and diallylamine. Tertiary amines such as triethylamine are technically operable for use in the process, but are less effective catalysts and require excessive reaction times to obtain suitable yields. They are therefore not preferred for use in the invention.

In general, primary amine catalysts such as n-Butylamine and ethanolamine give yields superior to those obtained with secondary amines such as diallylamine, morpholine or piperidine. These are, in turn, much superior to tertiary amines such as triethylamine, which require excessive reaction time to obtain suitable yields and are therefore not preferred for use in the invention.

The catalyst concentration is also a critical factor. If too low, the rate of the reaction is impractically slow and if too high, the rate of curcumin degradation becomes unacceptable. If all of the amine is charged at the beginning of the reaction, its concentration should be between 0.015M and 0.50M, and preferably between 0.15M and 0.19M.

A preferred method of operation, in order to minimize curcumin degradation while at the same time carrying the reaction to completion at a reasonable rate, is to add the amine throughout the course of the reaction, with the total amount of amine added preferably in the range of 20–45 mole % of the pentanedione employed.

Water Scavenger

Water is produced during the reaction upon formation of the diketone complex as well as upon formation of curcumin itself. Water in the reaction systems, irrespective of its source, can react with the diketone complex in the reaction mixture and thus substantially reduce the yield of curcumin. If too much water is present, the reaction will not proceed. Therefore, it is preferred, as nearly as possible, to carry out the process of the invention under anhydrous conditions.

To accomplish this, it is desirable to incorporate a scavenger into the reaction system which will bind with the water and prevent its reaction with the diketone complex. Suitable scavengers for this purpose have been found to be $C_{1-5}$ alkyl borates and $C_{1-5}$ alkyl phosphates and mixtures thereof. Another class of water-reactive compounds which has been used successfully is ketals, such as 2,2-dimethoxypropane. It is, of course, essential that such scavengers otherwise be substantially non-reactive with other components of the reaction system.

The relative yields of curcumin as a function of the mole ratios of tri-n-butyl borate to 2,4-pentanedione are tabulated in Table V of the Examples. The use of trimethyl borate is taught in our preferred embodiment (Example 1). The use of 2,2-dimethoxypropane as a scavenger is shown in Example 47. This should be added to the list in Table V. Other ketals would presumably be equally effective.

Process Variables

Enol Formation: The enolic diketone complex is easily made by admixing the two components—the diketone and a soluble complexing agent such as boric oxide or $C_{1-5}$ alkyl borate. The complex formation can be carried out at an elevated temperature. Besides boron, various other metals in soluble form are also known to form chelates with the curcuminoids. These include Zn, Sn, Al, Cu, Ni, Fe, Mo, W, Ti, Zr, Hf, Ba, Ca, Mg, Ta and U. The effectiveness of these soluble metal compounds as complexing agents will depend upon the solubility of the chelates in the reaction mass and the stability of these complexes under the conditions of the reaction.

The overall reaction rate between the aromatic aldehyde and the diketone complex is temperature related. Below about 40° C. the reaction is impractically slow for most applications. The reaction can, however, be carried out at higher temperatures so long as the reactants are maintained in the liquid phase and are not thermally degraded. It is preferred that the maximum temperature not exceed about 110° C. It is not necessary to carry out the process at elevated pressures. Atmospheric pressure is therefore preferred.

The concentration of the reactants may be varied over a fairly wide range in this process. As illustrated in Table VI, the initial pentanedione concentration will normally be in the range from about 0.14M to 2.5M, and preferably between 0.3M and 1.4M. At concentrations above about 2.5M the yield of product falls significantly due to the growth of side reactions. At very low concentrations, the volumetric efficiency of the process becomes impractically low, and the rate of the reaction becomes slow.

EXAMPLES

Example 1

A Preferred Embodiment

Vanillin (213 g, 1.40 mole) and boron oxide (46.6 g, 0.669 mole) were charged to a 1 L resin flask equipped with a heating mantle, thermometer and thermowatch, mechanical stirrer, condenser, and an additional funnel. The flask was maintained under a nitrogen blanket and was protected from light by use of an aluminum foil shield.

To this mixture was then added 320 mL (300 g) of N,N-dimethylacetamide (DMAC), 70.2 g (0.701 mole) of 2,4-pentanedione, and 145.5 g (1.40 mole) of trimethyl borate, and the mixture was heated, with stirring to 80° C. The condensation was begun by the addition of n-Butylamine (21.3 g, 0.291 mole) dropwise over the course of about 2 hours. (An initial exotherm is observed; the temperature should not be allowed to exceed 100°0 C.)

The course of the reaction was followed by high performance liquid chromatography (HPLC). After about three hours the reaction was judged complete as shown by disappearance of the intermediate product, feruloylacetone, from the chromatogram. The reaction was then terminated by pouring the reaction mass in a thin stream into 2 L of hot (60° C.) vigorously stirred 5% aqueous acetic acid.

The crude product initially appeared as a heavy oil; but as stirring continued, it slowly transformed into a dark red crystalline solid. After about one hour of stirring, the solids were filtered and resuspended in 2 L of water at room temperature. Following this water wash, the crude curcumin solids were collected once again. The dry weight of crude material from a typical synthesis was approximately 230 g; curcumin content was 77.2% (69.3% of theory).

The crude product was recrystallized by dissolving it in 4.8 L of boiling 75% aqueous acetonitrile, filtering and cooling it one-night in the refrigerator. The yield of chromatographically pure material was 136.4 g (53% of theory). Another 34 g (13.2% of theory) was retained in the supernatant liquid; this can be collected as a second crop.

Examples 2–14

Various Solvents

Vanillin (2.6 g, 0.017 mole), boron oxide (0.60 g, 0.0086 mole), and 2,4-pentanedione (0.87 g, 0.0087 mole) were charged to a reaction tube containing 4.0 mL of N,N-dimethylacetamide (DMAC). The mixture was heated, with stirring, to 80° C. n-Butylamine (0.2 mL, 0.15 g, 0.0020 mole) was then added and the mixture was held at 80° C.

The course of the reaction was followed by removing samples at intervals and analyzing the curcumin by HPLC, and also by spectrophotometric measurement of the curcumin absorption at 420 μm. After two hours the curcumin concentration in the reaction mass was 19.6%, corresponding to a yield of 49.1% of theory. A number of other solvents were screened by this procedure. The curcumin yields with these solvents are tabulated in Table I along with their respective dielectric constants, ε, measured at 20° C. unless otherwise noted.

TABLE I

| Example | Solvent | Curcumin Yield % of Theory | ε |
|---|---|---|---|
| 2 | N,N-Dimethylacetamide | 49.6 | 38.9 |
| 3 | N,N-Dimethylformamide | 50.5 | 38.3 |
| 4 | 1-Methyl-2-pyrollidinone | 50.1 | 32.6 |
| 5 | Dimethyl sulfoxide | 43.8 | 47.2 |
| 6 | Tetramethylene sulfone | 25.2 | 43.3[30] |
| 7 | 1,4-Dioxane | 20.7 | 2.22 |
| 8 | Acetonitrile | 17.5 | 36.6 |
| 9 | 2-Ethoxyethyl ether | 17.1 | — |
| 10 | Ethyl acetate | 13.7 | 6.08 |
| 11 | Ethanol | 9.5 | 25.3 |
| 12 | Butyl acetate | 5.9 | 5.07 |
| 13 | Nitromethane | 5.3 | 37.3 |
| 14 | Toluene | 2.5 | 2.38[23] |

Examples 15–21

Various Amines

Vanillin (2.6 g, 0.017 mole), boron oxide (0.60 g, 0.0086 mole), 2,4-pentanedione (0.87 g, 0.0087 mole) and 4.0 mL of N,N-dimethylacetamide were charged to a reaction tube and heated, with stirring, to 80° C. n-Butylamine (0.15 g, 0.0020 mole) was then added, and the stirred mixture was held at 80° C.

The course of the reaction was followed by removing samples at hourly intervals and measuring the curcumin concentration in the reaction mass spectrophotometrically. After 4 hours the curcumin concentration in the reaction mass was 20.7%, corresponding to a yield of 52.4% of theory.

Several other amine catalysts were screened by this procedure, using the same molar quantity of amine in all cases. The curcumin yields are tabulated in Table II, along with the $pK_a$ values of the amines.

TABLE II

| Example | Amine | Curcumin Yield % of Theory | $pK_a$ |
|---|---|---|---|
| 15 | n-Butylamine | 52.4 | 10.77 |
| 16 | Ethanolamine | 28.6 | 9.50 |
| 17 | Diallylamine | 17.2 | — |
| 18 | Morpholine | 16.8 | 8.33 |
| 19 | Piperidine | 4.9 | 11.12 |
| 20 | Triethylamine* | 0.9 | 11.01 |
| 21 | None | 0.07 | — |

*run in dimethyl sulfoxide

Examples 22–28

Boron Complexing Agents

Vanillin (2.6 g, 0.017 mole), boron oxide (1.20 g, 0.0172 mole), 2,4-pentanedione (0.87 g, 0.0087 mole), and 4.0 mL of N,N-dimethylacetamide were charged to a reaction tube and heated, with stirring, to 80° C. n-Butylamine (0.15 g, 0.0020 mole) was then added, and the stirred mixture was held at 80° C.

The course of the reaction was followed by removing samples at hourly intervals and measuring the curcumin concentration in the reaction mass spectrophotometrically. After 3 hours, the curcumin concentration in the reaction mass was 17.7%, corresponding to a yield of 48.3% of theory. Other boron complexing agents and other relative amounts of boron oxide were screened by this procedure. The curcumin yields are tabulated in Table III.

TABLE III

| Example | Complexing Agent | Mole Ratio of Complexing Agent to Pentanedione | Curcumin Yield, % of Theory |
|---|---|---|---|
| 22 | Boric oxide, $B_2O_3$ | 2 | 48.3 |
| 23 | Boric oxide, $B_2O_3$ | 1 | 52 |
| 24 | Boric oxide, $B_2O_3$ | 0.33 | 26.8 |
| 25 | Boric oxide, $B_2O_3$ | 0.1 | 14.3 |
| 26 | Boric acid, $H_3BO_3$ | 2 | 5.0 |
| 27 | Tri-n-butyl borate | 2 | 58.2 |
| 28 | None | 0.0 | 0.4 |

Examples 29–31

Effect of Water

The procedure described in Example 23 was utilized to test the effect of adding additional water to the reaction mass prior to initiation of the condensation reaction. The curcumin yields vs. water added are tabulated in Table IV.

TABLE IV

| Example | Mole Ratio of Water to Pentanedione | Curcumin Yield, % of Theory |
|---|---|---|
| 23 | 0 | 52 |
| 29 | 0.96 | 19.8 |
| 30 | 1.96 | 7.9 |
| 31 | 4.95 | 2.2 |

Examples 32–38

Dehydrating Agents

The procedure described in Example 23 was utilized to test the effect of adding dehydrating agents to the reaction mass prior to initiation of the condensation reaction. The dehydrating agent and its mole ratio relative to 2,4-pentanedione are tabulated in Table V.

TABLE V

| Example | Dehydrating Agent | Mole Ratio of Dehydrating Agent to Pentanedione | Curcumin Yield % of Theory |
|---|---|---|---|
| 23 | None | 0 | 52 |
| 32 | Tri-n-butyl borate | 0.1 | 56.4 |
| 33 | Tri-n-butyl borate | 0.2 | 57.5 |
| 34 | Tri-n-butyl borate | 1.02 | 64.6 |
| 35 | Tri-n-butyl borate | 2.02 | 67.8 |
| 36 | Tri-n-butyl borate | 4.02 | 73.2 |
| 37 | Triethyl phosphate | 1.98 | 54.0 |
| 38 | Triethyl borate | 1.98 | 71.6 |

Examples 39–41

Reactant Concentrations

The procedure described in Example 23 was utilized but with varying amounts of DMAC. The resulting reactant concentrations, relative to that in Example 23, are tabulated vs. yield of curcumin in Table VI.

TABLE VI

| Example | Ratio of Reactant Conc. Relative to Conc. in Ex 23 | Curcumin Yield, % of Theory |
|---|---|---|
| 23 | 1.0 | 52 |
| 39 | 2.0 | 13.6 |
| 40 | 0.33 | 55.2 |
| 41 | 0.1 | 32.7* |

*The reaction was very slow; curcumin production was still proceeding at a substantial pace after 3 hours when the run was terminated.

Examples 42–43

Different Temperature

The procedure described in Example 1 was also carried out at 60° C. and at 100° C. The maximum curcumin yields achieved in the reaction mass and the times to attain these yields are tabulated vs. temperature in Table VII. It should be noted that at 100° C. the curcumin content of the reaction mass reached a maximum after approximately 40 minutes and then began to drop as side reactions consumed the product; over the next 40 minutes, approximately 42% of the curcumin initially produced disappeared.

TABLE VII

| Example | Reaction Temp., °C. | Max. Curcumin Yield, % of Theory | Time to Attain Max. Yield, Min. |
|---|---|---|---|
| 1 | 80 | 77.2 | 180 |
| 42 | 60 | 79.9 | 160 |
| 43 | 100 | 73.4 | 40 |

Example 44

Synthesis of Didemethoxycurcumin

A 1 L reactor was charged with 171 g of 4-hydroxybenzaldehyde, 46.6 g boron oxide, 300 g N,N-dimethylacetamide, 70.2 g 2,4-pentanedione and 145.5 g triethyl borate. The mixture was stirred and heated to a temperature of 80° C. under nitrogen. n-Butylamine totaling 21.3 g was then fed dropwise into the reaction mixture over a period of 60 minutes. The temperature of the reaction mixture varied between 80° and 85° C. during this period.

Samples were taken throughout the run for analysis by HPLC. The chromatograph indicated disappearance of 4-hydroxybenzaldehyde and the appearance and growth, with time, of didemethoxycumumin.

The reaction was stopped after 103 minutes. The reaction mass was poured into 4 L of hot 5% acetic acid with stirring. After about 2 hours, the mixture was decanted. The solids remaining were broken up into smaller particles and treated with 2 L of water for 2 hours. After filtration, the crude product amounted to 265.5 g with a purity of 76.4% didemethoxycurcumin.

The crude product was dried overnight in a vacuum oven at 45°–50° C. A 55 g portion of the product was dissolved in 1 L of 75% acetonitrile/25% water at reflux, filtered hot and then recrystallized in a refrigerator at 2° C. over a period of two days. The resultant crystalline product, weighing 24.9 g, had a purity of 100% didemethoxycurcumin.

Example 45

Synthesis of Ethyl Curcumin

A 1 L reactor was charged with 233 g of 3-ethoxy-4-hydroxybenzaldehyde (ethyl vanillin), 46.6 g boron oxide, 300 g N,N-dimethylacetamide, 70.2 g 2,4-pentanedione and 145.5 g trimethyl borate. The mixture was heated to 70° C. with stirring under nitrogen. n-Butylamine (21.3 g) and dimethylacetamide (20 g) were added dropwise over a period of 100 minutes. The temperature rose to 85° C. during addition and then fell to 72°–74° C. after cooling was applied. The product was a thick paste.

Samples were taken throughout the run for HPLC analysis which showed that 87.6% of the ethyl vanillin was reacted.

The crude reaction mixture was mixed into 4 L of hot (65° C.) 5% acetic acid, mixed for about 2 hours and placed in a refrigerator at 6° C. overnight. The cold reaction product was filtered to yield 406 g of solids which were dried in a vacuum overnight at 47° C. to yield 298.7 g crude product, which was found to contain about 72% ethyl curcumin.

A 75 g portion of the crude product was dissolved in 650 mL, 75% acetonitrile/25% water at reflux, filtered and then recrystallized in a refrigerator over a weekend. The resultant yellow slurry was filtered and dried, and yielded 52.5 g ethyl curcumin having greater than 99% purity.

Example 46

Synthesis of "Natural Curcumin"

A 1 L reactor was charged with 182.6 g vanillin, 24.4 g 4-hydroxybenzaldehyde, 46.6 g boron oxide, 300 g dimethylacetamide, 70.2 g 2,4-pentanedione and 145.5 g trimethyl borate. The mixture was heated to 70° C. with stirring under nitrogen. Over a period of 100 minutes, 21.3 g of n-Butylamine was added dropwise. During the amine addition, the temperature rose to 80° C. and then decreased to 72° C.

The reaction was stopped at 140 minutes at which point no further change in curcuminoid content was observed. Samples were taken throughout the run for HPLC analysis. The reaction mass was poured into 4 L of 5% aqueous acetic acid held at 60° C. After 2 hours, it was decanted and the acid replaced with 2 L water and refrigerated overnight. The solids were filtered off and dried in an oven at 45° C. for 1 hour (verified 264 g with an assay of 72% curcuminoids).

An aliquot of 91 g of the crude product was dissolved in 500 mL of 75% acetonitrile/25% water at reflux, filtered hot and recrystallized in a refrigerator overnight, filtered and dried. A dark orange powder weighing 30.0 g was obtained which contained 68% curcumin, 27% demethoxycurcumin and 5% didemethoxy-curcumin. No other peaks were observed in the HPLC analyses except the tautomers of the curcuminoids. From these results, it can be seen that by controlling the ratio of the benzaldehydes in the reaction mixture, a broad range of compositions similar to "natural" curcumin can be obtained.

Example 47

Synthesis of Curcumin

In this Example, curcumin was made by substantially the same procedure as Example 1, but with the substitution of 2,2-dimethoxypropane in place of trimethyl borate as water scavenger for the reaction.

A 1 L reactor was charged with 213 g vanillin, 46.6 boron oxide, 300 g dimethylacetamide, 70.2 g 2,4-pentanedione and 145.8 g 2,2-dimethoxypropane. The mixture was stirred and heated to a temperature of 70° C. under nitrogen. n-Butylamine totaling 21.3 g was added dropwise over a period of 100 minutes. The temperature of the reaction mixture varied between 70° C. and 75° C. during this period. Samples of the reaction mixture were taken throughout the run for analysis by HPLC.

The reaction was allowed to proceed for 127 minutes, with some loss of curcumin being observed after 80 minutes. The reaction mass was poured into 4 L of hot aqueous 5% acetic acid and allowed to cool 1.5 hours, after which it was decanted and mixed with 2 L of water and refrigerated for two days. At the end of that time, solids weighing 487 g were separated by filtration. An aliquot of the solids weighing 114 g was dissolved in 500 mL of 75% acetonitrile/25% water at reflux, cooled and recrystallized overnight in a refrigerator. A total of 41.6 g of solids were obtained which had a purity of over 99% curcumin.

What is claimed:

1. A process for the synthesis of curcumin-related compounds comprising the sequential steps:

A. In a chemically inert, highly polar, aprotic solvent, reacting a suitable complexing agent with a 2,4-diketone of the general structure $RCH_2$—CO—$CH_2$—CO—$CH_2R$ in order to produce a stable enolic reactant with the general structure $RCH_2$—C(OH)=CH—CO—$CH_2R$, in which the R groups are independently selected from H and $C_{1-12}$ hydrocarbyl groups selected from alkyl, aryl, aralkyl, alkaryl groups and mixtures thereof;

B. To the reaction from step A, adding aromatic aldehyde in sufficient amount to effect complete reaction of all of the stable enolic reactant in the solution;

C. While maintaining the liquid solution from step B at a temperature of at least 40° C., admixing therein catalyst selected from the group consisting of organic primary amines, secondary amines and mixtures thereof to effect condensation of the aldehyde with the enolic reactant, with the concomitant formation of curcumin-related compound, intermediate compounds, water and other reaction by-products and continuing the reaction until all of the enolic reactant in the reaction mass has been consumed, provided further that (1) if the amine catalyst is added incrementally, the total amount thereof is 20–45 mole percent of the enolic reactant or (2) if the entire amine catalyst is added at the beginning of step (1), the concentration thereof is 0.015–0.50 molar;

D. Admixing the reaction mass from step C with dilute aqueous acid to effect neutralization of any organic amine catalyst which is present, precipitation of the curcumin-related compound in crystalline form and solubilization of unreacted materials; and E. Separating the precipitated curcumin-related compound from the acidic reaction mass of step D.

2. The process of claim 1 in which the precipitated curcumin-related compound is washed with aqueous solvent to remove adsorbed solvent and reaction by-products therefrom.

3. The process of claim 2 in which the washed curcumin-related compound is redissolved in solvent and recrystallized therefrom to effect further purification of the crystallized curcumin-related compound.

4. The process of claim 3 in which the recrystallization solvent is aqueous acetonitrile.

5. The process of claim 3 in which the recrystallization solvent is aqueous ethanol.

6. The process of claim 1 in which a water scavenger is added to the reaction mass of step B to effect scavenging of water produced in the reaction.

7. The process of claim 6 in which the water scavenger is selected from the group consisting of $C_{1-5}$ alkyl borates, $C_{1-5}$ alkyl phosphates and mixtures thereof.

8. The process of claim 6 in which the scavenger is a molecular sieve in which any water in the reaction mass is adsorbed selectively.

9. The process of claim 1 in which the highly polar, aprotic solvent is an organic amide.

10. The process of claim 9 in which the solvent in the reaction solution is N,N-dimethylacetamide.

11. The process of claim 1 in which the enolate is a complex of the diketone with boric oxide.

12. The process of claim 1 in which the enolate is a complex of the diketone with $C_{1-5}$ alkyl borate.

13. The process of claim 1 in which the molar ratio of carbocyclic aldehyde to acetylacetone is at least 1.8.

14. The process of claim 1 in which the organic amine catalyst is diallylamine.

15. The process of claim 1 in which the organic amine catalyst is n-Butylamine.

16. The process of claim 1 in which the organic amine catalyst is morpholine.

17. The process of claim 1 in which the carbocyclic aldehyde is vanillin and the primary reaction product is curcumin.

* * * * *